(12) United States Patent
Zdrahala et al.

(10) Patent No.: US 6,299,448 B1
(45) Date of Patent: Oct. 9, 2001

(54) SURGICAL IMPLANT SYSTEM FOR RESTORATION AND REPAIR OF BODY FUNCTION

(76) Inventors: Ivanka J. Zdrahala; Richard J. Zdrahala, both of 6825 Stonewood Ct., Eden Prairie, MN (US) 55346

( * ) Notice: Subject to any disclaimer, the term of this patent is extended or adjusted under 35 U.S.C. 154(b) by 0 days.

(21) Appl. No.: 09/505,567

(22) Filed: Feb. 17, 2000

Related U.S. Application Data

(60) Provisional application No. 60/120,405, filed on Feb. 17, 1999.

(51) Int. Cl.⁷ .................................................... A61C 8/00
(52) U.S. Cl. ...................... 433/173; 433/175; 433/215; 623/23.48
(58) Field of Search ................... 433/173, 215, 433/218, 175; 623/16.11, 17.18, 23.98, 23.52, 1.18, 1.19, 1.22

(56) References Cited

U.S. PATENT DOCUMENTS

| | | | |
|---|---|---|---|
| 4,252,525 | * 2/1981 | Child | 433/173 |
| 5,015,183 | 5/1991 | Fenick . | |
| 5,211,658 | * 5/1993 | Clouse | 623/1.22 |
| 5,219,287 | * 6/1993 | Mishihara | 433/173 |
| 5,951,288 | * 9/1999 | Sawa | 433/173 |
| 6,042,380 | * 3/2000 | De Rowe | 433/173 |
| 6,162,244 | * 12/2000 | Braun et al. | 623/1.22 |

* cited by examiner

*Primary Examiner*—Todd E. Manahan
(74) *Attorney, Agent, or Firm*—Hoffmann & Baron, LLP

(57) ABSTRACT

The present invention relates generally to surgical implants intended for the augmentation, repair, and restoration of soft tissue (e.g. gingiva or cartilage), hard tissue (e.g. bone), and the like. More particularly, the present invention relates to the in vivo anchoring of cast implants by stent-like anchors made of a shape memory alloy and/or polymers which are desirably covered with a textile sleeve of a specific porosity.

32 Claims, 1 Drawing Sheet

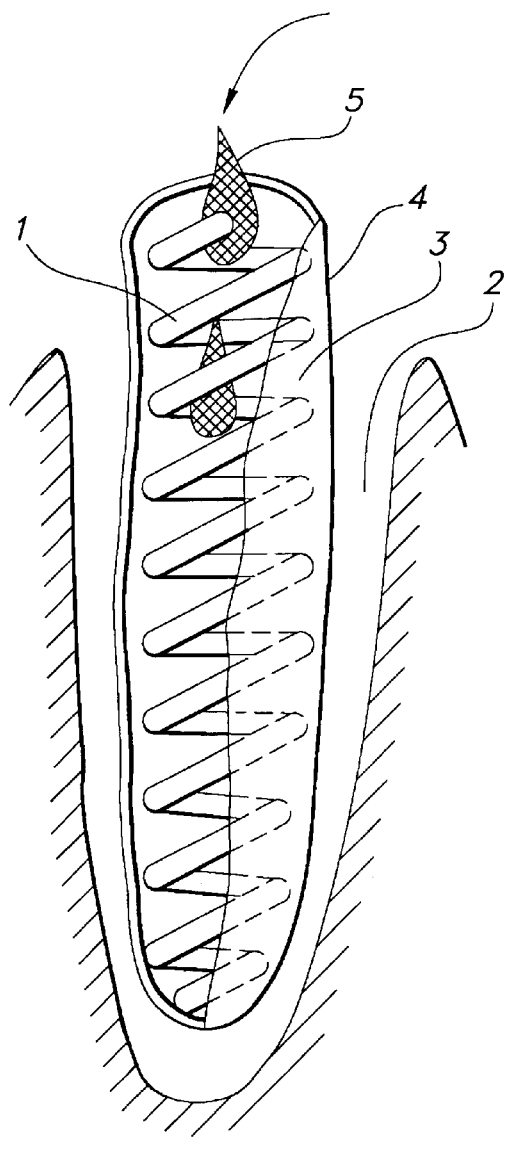
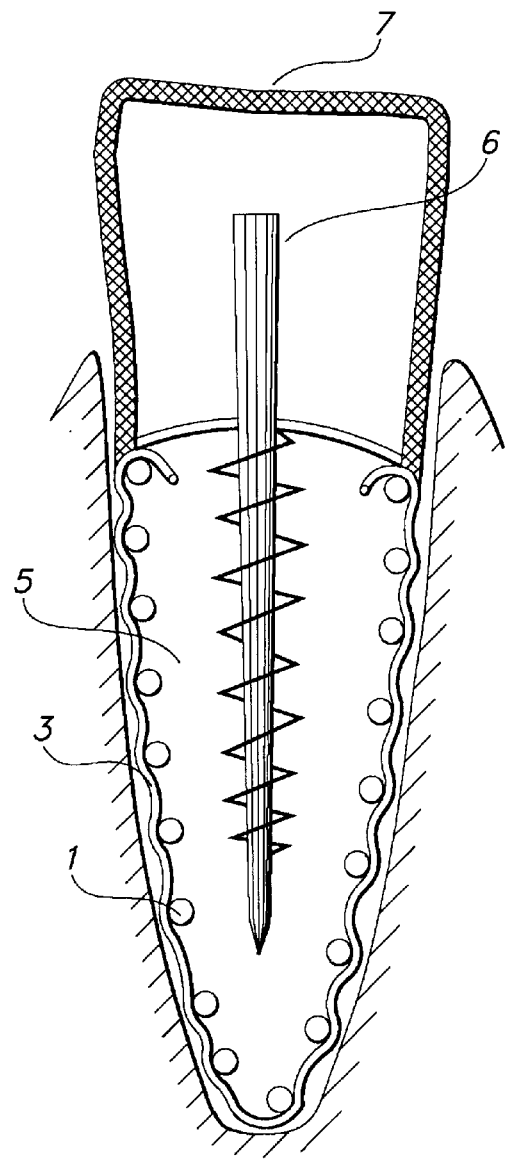
FIG 1     FIG 2

SURGICAL IMPLANT SYSTEM FOR RESTORATION AND REPAIR OF BODY FUNCTION

This application claims the benefit of U.S. Provisional Application No. 60/120.405, filed on Feb. 17. 1999.

FIELD OF THE INVENTION

The present invention relates generally to surgical implants intended for the augmentation, repair, and restoration of soft tissue (e.g. gingiva or cartilage), hard tissue (e.g. bone), and the like. More particularly, the present invention relates to the in vivo anchoring of cast implants by stent-like anchors made of a shape memory alloy and/or polymers which are desirably covered with a textile sleeve of a specific porosity. The in vivo cast implants are formed using reaction injection molding (RIM) amenable polymers or similar in vivo polymerized reactive polymer systems which are introduced into the anchor assembly positioned in natural body cavities (such as those which exist after tooth extraction) or in man-made holes, such as in orthopedic surgical procedures.

BACKGROUND OF RELATED TECHNOLOGY

The present invention is desirably used in minimally invasive procedures such as restorative dentistry and arthroscopy.

As the lifespan of people has increased, so to has the need for permanent dental replacements. Restorative dentistry encompasses efforts to conserve and restore decayed, defective, missing, and traumatically injured teeth, thereby promoting the dental health and achieving the aesthetic desires of the patient.

In the dental field, polymers are recognized as important components of composite restorative materials.

Methods and devices for the delivery and cure of materials within the oral cavity are known. For example U.S. Pat. No. 4,368,040 to Weissman ("Weissman") discloses a preparation of dental prostheses which relies on the use of molds of body parts in order to cast or otherwise form prosthetic replacement parts. U.S. Pat. No. 5,156,777 to Keye ("Keye") discloses the use of three-dimensional data obtained from an organ site to prepare a life-size model of an organ site, which in turn is used to cast a prosthetic implant.

Further, U.S. Pat. No. 5,015,183 to Fenick ("Fenick") discloses a preformed dental stent and a method of use which includes taking a negative impression of a patients tooth which is to be augmented and restored in order to provide a guide for drilling the cavity for a repair. This concept is utilized in a variety of applications to assist with positioning and fixation of dental implant, predominantly into an original tooth, as seen in U.S. Pat. No. 5,133,660 to Fenick, U.S. Pat. No. 5,246,370 to Coatoam, U.S. Pat. No. 5,320,529 to Pompa, U.S. Pat. No. 5,350,297 to Cohen, and U.S. Pat. No. 5,613,852 to Bavitz.

A problem with dental implants is that they are rather invasive and occasionally rejected by the body and expelled from the implantation site, such as the tooth socket (alveolus), referred to hereinafter as the "cavity". Another concern is that current techniques employ repetitive surgery, implantation, healing and correction of the prosthesis. These procedures are typically repeated as may times as necessary to achieve the desired dental prosthesis implantation to the bone, as well as the appropriate stabilization. Consequently, these techniques are typically associated with a great deal of pain and inconvenience to the patient, as well as with the expenditure of excessive efforts and time by the oral surgeon, thereby resulting in higher treatment costs.

Therefore, exists a need for a device, such as a dental prosthetic, and a method for the implantation of the device that not only enhances the opportunity for fixation of the device in the desired location, thereby increasing the functionality of the device, but also eases the pain, discomfort, inconvenience and cost realized by both the patient and the dental surgeon. The present invention is directed towards meeting these and other needs.

SUMMARY OF THE INVENTION

Accordingly, in one aspect of the present invention there is provided an improved implantation method and device for augmentation, repair and restoration of teeth, bone, cartilage and similar tissues.

In another aspect of this invention there is provided a stent-like anchor, such as a coil, helix, mesh, tube and device of similar geometry which is made of one or more memory shape alloys and which are covered by porous materials formed into a sleeve or similar covering, to affect fixation and stabilization of an implant into a cavity. The utilization of coverings of selected porosity stimulates ingrowth of soft or hard tissues surrounding the implant, thereby promoting healing and immobilization of the prosthetic device. The stent-like anchor and porous covering are herein known as the "stent assembly".

In yet another aspect of the present invention there is provided sustained delivery of medicine or biologically active species for therapeutic or tissue ingrowth control by the release of the medicine or biological species from the coating of the porous covering. Alternatively, the medication or biological species may be incorporated within the porous covering.

In yet another aspect of the present invention there is provided an improved restoration method and system by including an in vivo cast implant using RIM-amenable or similar in vivo formed and/or polymerized material. Such material fills an alveolar or other cavity lined by the stent-assembly. The polymerization of the RIM-amenable material and its in vivo formation produces heat. This exothermic reaction triggers the shape memory function within the stent material to shape it into a tight fit within the cavity.

In yet another aspect of the present invention there is provided the placement and casting in of an additional securement device such as an anchor, post or pin. This is desirably added contemporaneously with delivery of the RIM-amenable material, in order to provide additional functionality to the implant, such as the ability to attach a crown.

The present invention is desirably used for the implantation of a prosthetic device, such as, for example, the replacement of a tooth following the total extraction of a diseased tooth. Such restorative dentistry as used in the present invention is desirably accomplished through a minimally invasive surgical procedure.

BRIEF DESCRIPTION OF THE DRAWINGS

FIG. 1 is a perspective view of a dental implant device of the present invention showing a covered coil in the unexpanded position in alveolar cavity.

FIG. 2 is a cross-section of a dental implant device of the present invention showing the covered coil portion in the expanded state and further including a post and crown.

DETAILED DESCRIPTION OF THE INVENTION

In the present invention, a four-part system is desirably utilized in which a stent-like device composed of shape memory material is designed to fit within a cavity or lesion. The device is then covered with medical grade fabric or similar porous material to form sleeve-like covering. The porosity of this material is conducive to the application of the device and the tissue surrounding it. The porous material may also be coated or impregnated with a medicine or attachment-inducing bioactive species to heal and further promote or control the ingrowth of surrounding tissue.

Upon positioning of the stent device or assembly within the cavity, an RIM-amenable material is delivered to the implant site. A two- or more component system in a two- or more barrel syringe is mixed by, for example by a Kenix™-type static mixer, delivered by cannula or the like to the implant site and reacted within the stent-like assembly. The exothermic reaction of material formation triggers the memory shape behavior of the stent and expands the filled stent within the implant cavity.

An implant of the present invention, its components and positioning in the body are illustrated in FIGS. 1 and 2. Turning to FIG. 1, a stent-like device 1 of appropriate functional shape or design and based on shape memory alloy (SME) material is used to anchor and position a dental implant within an alveolar cavity 2. Materials such as Nitinol™ and the like, both in standard or super-elastic form, may be used. The use of polymers is also contemplated. Stent-like device 1 is laserably radially expandable to provide a tight fit in the implant cavity. It may take the form of a coil, a tubular configuration, a mesh-like, a helix or other radially expandable form.

A Nitinol™ wire with O.D. of 0.011" to 0.025" is formed to coil, helix, counter-helix, mesh tube or a similar conformation to provide as a basis for stent-like assembly 4. Biodurable polymers (e.g. crystalline or highly oriented PE, PP, PMMA, polyesters and polyamides) are desirably used, but biodegradable materials may also be used in certain applications. Materials such as polylactides(PLA), polyglycolides (PGA) and their copolymers (specifically PLA/PGA systems differing in the temperature range of shape changing transitions), polyamides and polyurethanes are contemplated. These materials are extruded into monofilaments, hollow fibers or tubes and are formed into any suitable and desirable shape, desirably similar to those based on Nitinol™ wire.

In a desired aspect of the present invention, a stent-like device 1 is provided which conforms, in its expanded state, to the parameters of cavity 2. Due to the memory shape function of the stent, a method of designing such stent assembly requires only approximate measurements of dimensions of the cavity to be implanted. As shown in FIG. 1, based upon the parameters of the cavity 2 to be filled, the stent-like device 1 is designed, in its smaller arrangement, prior to expansion to approximate a functional shape or design. The actual dimensions of the cavity will be within the range of expansion of the shape memory alloy material in order that the stent will be properly positioned and anchored within cavity 2. As shown in FIG. 2, an appropriate fit of stent 1 within the cavity 2 is achieved by a temperature-triggered dimensional change, such as expansion. This ability of the stent I lends the present invention to the efficient development of a series of implants within a range of dimensions which are suitable for implantation.

In another desired aspect of the present invention, a stent-like device 1 is covered with a porous fabric 3 or similar material having a precisely defined porosity, thereby forming a sleeve suitable for tissue attachment. The combination of the stent-like device 1 and sleeve 3 is known herein as stent assembly 4. A thin fibrous film or fabric with porosity determined by water permeability is desirably used as the covering. Desirably, the porosity is in the range of 50 to 5000 ml/min/cm2, and more desirably, 100 to 3000 ml/min/cm2. This porosity allows for rapid tissue ingrowth and incorporation, thereby allowing the device to be anchored in place. The fabric can be a weave, knit or nonwoven. Additionally, the fabric thickness is desirably no greater than about 1 mm, and more desirably no greater than about 0.2 mm.

Typically, a thin fabric will heal-in more quickly than a thicker fabric. The fabric can be comprised of non-resorbable or resorbable fibers, or a combination thereof. Fibers that are made from polyester, polyethylene terepthalate, polypropylene, polyethylene, polyurethane, polytetrafluoroethylene, polyglycolic acid (PGA), polylactic acid (PLA) or some other suitable polymer, and blends thereof, can be employed. Additionally, the fabric can be treated with natural or synthetic resorbable coatings, such as collagen, polyvinyl alcohol (PVAL), hydrogels, etc. to achieve a lower initial porosity implant which, due to bioresorption over time, subsequently increases the porosity of the fabric, thereby promoting tissue attachment and fixation. Further, the sealants can be used to control the rate of healing and tissue incorporation through the wall of the fabric.

Polyester, polyamide, biodurable polyurethane and ePTFE materials are illustrative of materials which can be used as a covering material. Desirably, DACRON polyester is used. The material's porosity, or its gradient, is selected in accordance with a particular application in accordance with the specific tissue ingrowth necessary to stabilize and heal the implant. A combination of biodurable and biodegradable materials can be used for the sleeve or covering to provide sustained formation of pores, for step-wise tissue ingrowth and to differentiate between and provide for hard and soft tissue ingrowth.

The covering may be used as a reservoir for tissue growth drugs and biologically active compounds, may be incorporated therein as well as additional impregnation materials such as hydrogels. The use of materials such as hydrogels allows for the sustained and controlled release of a drugs and other therapeutic materials. Use of drugs and healing-mediating biologicals such as antibiotics, aspirin, novocaine, Transforming-Growth-Factor-Beta (TGF-Beta), Osteogenic Proteins OP-1 and OP-2, Bone Morphogenic Proteins (BMP), desirably BMP-1 and BMP-2 and, desirably, the recombinant rhBMP-2, or BMP/OP combination for regeneration of both gum and bone tissue are also contemplated In another desired aspect of the present invention, the above components are positioned in the cavity 2 in situ or in vivo and a polymerizable biomaterial 5 is delivered. Polyurethanes (PU) or polymethyl methacrylate (PMMA) materials are desirably used. For PU, the Reaction Injection Molding (RIM)-amenable materials are desirably used and are delivered via methodology designed and implemented to do so. The RIM-amenable materials are desirable because RIM is based on molecular-scale impingement mixing of two or more streams of liquid co-reactive components as they enter mold, the stent assembly 4 lining the cavity in the present invention. This process results in the formation of a solid implant. Although the RIM-based procedure is desired, the use of a two- or more-barrel syringe, equipped with a static mixer and a delivery cannula is also suitable for use in the delivery procedure. A PMMA-based system may also be used.

Both PU and PMMA materials release a significant amount of heat during their polymerization. This reaction exotherm from in vivo and in situ polymerized materials represents another desired aspect of the present invention, triggering the shape memory expansion to provide initial anchoring via full contact of the device with the surface of the cavity 2, which is important for the start of the tissue ingrowth. Although the polyurethanes are desirably used because of their versatility, i.e., they offer a large number of structures and possess properties which render them excellent biomaterials, many other polymer systems may be used for the in vivo polymerizable biomaterials in the present invention.

As further shown in FIG. 2, an insert or post 6 used for tooth implantation may be embedded into an RIM-amenable or other in vivo or in situ polymerizable biomaterial 5 and may provide support for or a means of attachment for an artificial tooth surface such as crown 7.

In another aspect of the invention there is provided a dental implant device which includes a generally elongate radially expandable stent member at least partially covered by a porous polymeric sleeve formed from a fabric or film, said stent member being formed from a shaped memory material capable of expanding in the cavity of the implant site, said sleeve being adapted to receive a polymerizable material therein for providing internal structure and support to said implant device upon in situ cure.

In yet another aspect of the invention there is included a dental implant kit which includes: (i) a stent member; (ii) a sleeve member for covering said stent and for receiving in situ polymerizable polymer; and (iii) polymer components which when mixed can be delivered in vivo for in situ polymerization. Optimally, a post and dental crown may also be included in the kit.

Consequently, the present invention allows for the efficient replacement of a diseased tooth. This replacement is achieved without weakening or otherwise altering the surrounding teeth. The present invention allows for the maintenance of spacing between the teeth without the potential for gap shape changes, thus preventing bone deterioration. The present invention also allows for attachment of a crown for functional and/or cosmetic reasons.

The following examples are set forth as illustrative of the present invention and are in no way meant to limit the scope of the present invention.

EXAMPLE 1
Polymerizable Biomaterial Preparation

A 65 percent Hard Segment (HS) (HS is combined weight of isocyanate and chain extender) polyurethane system was formulated using 4,4'-diphenylmethane diisocyanate (MDI) and 1,4-butane diol (BDO) chain extender as Hard Segment intermediates and polytetramethylene ether glycol (PTMEG) molecular weight (MW) of 1000 daltons as the soft segment.

A preferred polymer system of the present invention was prepared using NCO-terminated all isocyanate-containing part "A" and all remaining intermediates such as OH-terminated polyols, chain extenders and all other additive components composing part "B", and was delivered, and cured in order to provide a useful biomaterial. Both free NCO (FNCO) and OH values needed for calculation of stoichiometry of polymerization were determined using conventional analytical techniques.

The following ingredients were obtained and mixed in the manner described below:
(a) 4,4'-diphenylmethane diisocyanate ("MDI") was obtained as Mondur ML from Bayer AG, Pittsburgh, Pa.
(b) PTMEG of molecular weight of 1000 daltons and 1,4-BDO were obtained from BASF Corporation, Mount Olive, N.J.
(c) A Cotin 222 tin catalyst was used as received from CasChem Co.,Bayonne, N.J.
(d) amine catalyst (triethylene diamine)DABCO S-25 from Air Products & Chemicals, Allentown, Pa.
(e) Vitamine E, RONOTECH 201, from Hoffmann-La Roche Paramus, N.J., in concentration of 0.1–0.2 weight percent per the total formulation was used as an antioxidant.

A catalyst, having both tin ester catalyst (COTIN 222) and triethylene diamine (DABCO S-25) components in a 1:2 ratio by weight, was used. This combination allows for delayed action, synergistic catalysis with a well defined induction/gellation kinetics profile. Such catalyst action is highly desirable to allow enough time for mixing, delivery and filling before the curing polymerization occurs quickly.

The isocyanate component, referred to as part "A", was prepared by melting the MDI flakes to 45 degrees C., filtering the solids on a Buchner funnel and degassing at approximately 20 mm Hg. It was kept at 45–50 degrees celcius oven prior to use.

Part "B", which contained the chain extender soft segment polyol, antioxidant and catalyst system was stirred in a resin kettle at 40 to 60 degrees C. until filly blended and slowly cooled to the minimum temperature to maintain all components liquid.

For assessment of reactivity and reaction exotherm, both components of the system were filled in required stoichiometry while kept liquid to mimic the RIM process. They were placed into a two-barrel syringe system of the type used for delivering two-part dental composites. They were then mixed and delivered through a KENIX™-type static mixer into a triple-insulated polystyrene cup "adiabatic" mold equipped with a suitable thermocouple. Approximately 3 ccm volume of mixed polymerizable components was used. The system, with initial staring temperature of 47 degrees celcius gelled within 15–20 seconds at 0.02 percent catalyst. The reaction exotherm of 100–130 degrees celcius was obtained.

In a similar way, a plaque of ⅛" thickness was cast into a teflon-coated mold and cured for several hours at 37–45 degrees celcius. All testing was performed in accordance with ASTM Testing Methodology and accepted standard laboratory procedures. The hardness, average load bearing capability and accelerated degradation were determined.

EXAMPLE 2
PMMA-based Material

The in vitro exotherms generated from the composition in Example 1 were compared to a PMMA-based bone cement. Approximately the same weight and relatively constant surface-to-volume ratio was used to assure comparability.

In vitro adiabatic cure exotherm was again measured in triple-insulated foamed polystyrene cup as in Example 1. The PMMA-based bone cement was mixed with activator in a plastic beaker and spooned by spatula to the cup/thermocouple assembly. The induction period was in excess of 400 seconds. When polymerized adiabatically, the bone cement produces approximately the same amount of heat. Polymerization in vivo of this material does not causes extensive tissue necrosis by excessive heat evolution.

EXAMPLE 3
Stent Assembly

A Nitinol wire of 0.011" O.D., from Anson Medical Ltd., Uxbridge, Middlesex, UK was wound into a 8 mm O.D. 15 mm long coil at a temperature for producing martensitic transformation and resultant microstructure. Then, the coil was cooled and reshaped into a 5 mm O.D. coil. A loosely pleated sleeve of approximately 5–6 mm O.D. and 20 mm in length, was made from Dacron™ fabric having a thickness of 0.3 mm and porosity of 450 ml/min/cm2. The 5 mm O.D. coil was placed into this sleeve and secured in place with a few sutures to form the stent assembly.

An approximately 7 mm I.D. hole, about 15 mm deep, was drilled into a bone model and the stent assembly was tucked into this hole. The bone model was preheated to 35–45 degrees celcius and the assembly was filled in a step-wise manner by the PU formulation of Example 1. Both coil and sleeve expanded to fill the predrilled hole within approximately 2–3 minutes. Relatively tight porosity of the sleeve prevented any leakage of PU material prior its polymerization. A mushroom like head from excess of material crowned the implant.

The present invention is particularly suited for use in restorative dental implants. It provides a porous media such as the fabric to negotiate and regulate both the soft tissue (gingiva) and the hard tissue (e.g. the jawbone) ingrowth. The prophylactic, bleeding control and pain killing medicines and tissue incorporation promoting agents are delivered from the fabric as reservoir. It further provides for the best possible contact between the tissues and the fabric by memory-shape stent-like anchor. The in vivo formed polymer with reaction exotherm is then provided to trigger the memory-shape action of the stent, to fill the space and to immobilize the post for crown attachment, if needed.

What is claimed is:

1. A method for restoration of dental tissue, and providing an implant device for attaching artificial teeth comprising the steps of:
   (i) preserving and dressing the cavity created by the extraction of a tooth;
   (ii) estimating or measuring the parameters of the cavity or lesion formed within the bone and gum tissues;
   (iii) providing a stent assembly comprising an expandable stent made from a shape-memory material, said stent having a sleeve of porous fabric at least partially covering said stent, said stent assembly generally conforming to the parameters of said cavity or lesion;
   (iv) positioning the said stent assembly within the cavity or lesion; and
   (v) delivering an in situ polymerizable, exothermic polymer system to the inner space of the said assembly to provide internal structure to the assembly.

2. The method of claim 1, wherein said expandable stent is formed from a shape-memory metal alloy.

3. The method of claim 1, wherein said expandable stent is formed from nitinol.

4. The method of claim 1, wherein the expandable stent is radially expandable.

5. The method of claim 1, wherein said expandable stent is in the shape of a helical coil.

6. The method of claim 1, wherein said expandable stent is in the shape of a tube having openings in its wall.

7. The method of claim 1, wherein said expandable stent is formed from a shape-memory polymer.

8. The method of claim 7, wherein said expandable stent is formed from a biodurable polymer.

9. The method of claim 7, wherein said expandable stent is formed from a biodegradable polymer.

10. The method of claim 1, wherein said sleeve is a knitted, woven, braided or non-woven fabric.

11. The method of claim 1, wherein said sleeve has a water porosity of about 50 to about 1,000 ml/min/cm$^2$.

12. The method of claim 1, wherein said sleeve has a thickness of about 0.1 to about 1.0 mm.

13. The method of claim 1, wherein said sleeve is formed of a combination of biodurable and biodegradable fibers.

14. The method of claim 1, wherein said sleeve is expanded PTFE.

15. The method of claim 14, wherein said sleeve has a fibril length of about 30 to about 300 microns.

16. The method of claim 14, wherein said sleeve has a thickness of about 0.1 to about 1.0.

17. The method of claim 1, wherein said sleeve is coated or impregnated with a bioactive material.

18. The method of claim 17, wherein said bioactive material is released from a hydrogel matrix.

19. The method of claim 1, wherein said delivering of said in situ polymerizable exothermic polymer system is by reaction injection molding.

20. The method of claim 1, wherein said in situ polymerizable exothermic polymer system includes a polyurethane or polyurethane-containing polymer.

21. The method of claim 1, wherein the in situ polymerizable exothermic polymer system includes a polymethylmethacrylate-based bone cement.

22. The method of claim 1, wherein the in situ polymerizable exothermic polymer system provides sufficient heat during polymerization to cause expansion of said expandable stent.

23. The method of claim 1, wherein said expansion of said expandable stent is sufficient to initially anchor said stent assembly.

24. The method of claim 1, further including the step of positioning within said in situ polymerizable exothermic polymer system a post for attaching a crown.

25. The method of claim 24, further including the step of attaching a crown to the exposed surface of the stent assembly.

26. A dental implant device comprising a generally elongate expandable stent member at least partially covered by a porous sleeve formed from a porous polymeric fabric or film, said stent member being formed from a shape memory material capable of expanding in the cavity of the implant site, said sleeve being adapted to receive a polymerizable material therein for providing internal structure and support to said implant device upon in situ cure.

27. The dental implant of claim 26, wherein the stent member is in the shape of a helical coil, porous tube or mesh-walled tube.

28. The dental implant of claim 26, wherein the sleeve is a material selected from biodurable materials, biodegradable materials and combinations thereof.

29. The dental implant of claim 26, further including a post for attachment of a crown.

30. The dental implant of claim 29, further including a crown for attachment to said post and implant device.

31. A dental implant kit comprising (i) a stent member; (ii) a sleeve member for covering said stent member and for receiving in situ polymerizable polymer and (iii) polymer components which when mixed can be delivered in vivo for in situ polymerization.

32. The dental implant kit of claim 31 further including a post and dental crown.

* * * * *